(12) United States Patent
Easter

(10) Patent No.: US 7,018,366 B2
(45) Date of Patent: Mar. 28, 2006

(54) VACUUM ASSISTED RELIEF SYSTEM (VARS)

(76) Inventor: William Craig Easter, 314 W. Franklin, Weatherford, OK (US) 73096

( * ) Notice: Subject to any disclaimer, the term of this patent is extended or adjusted under 35 U.S.C. 154(b) by 65 days.

(21) Appl. No.: 10/345,933

(22) Filed: Jan. 17, 2003

(65) Prior Publication Data

US 2004/0143229 A1   Jul. 22, 2004

(51) Int. Cl.
*A61M 1/00*   (2006.01)
(52) U.S. Cl. ............... 604/327; 604/544; 604/355
(58) Field of Classification Search ........... 604/544, 604/327–355, 385.01; 4/144.1, 144.2, 144.3, 4/144.4
See application file for complete search history.

(56) References Cited

U.S. PATENT DOCUMENTS

| | | | | |
|---|---|---|---|---|
| 2,749,558 A * | 6/1956 | Constantin et al. | ............ | 4/454 |
| 2,944,551 A * | 7/1960 | Breer | ............. | 604/73 |
| 3,349,768 A * | 10/1967 | Keane | ............. | 604/347 |
| 3,751,727 A * | 8/1973 | Shepard et al. | ............. | 2/2.14 |
| 4,610,675 A * | 9/1986 | Triunfol | ............. | 604/329 |
| 4,673,401 A * | 6/1987 | Jensen et al. | ............. | 604/353 |
| 4,692,160 A * | 9/1987 | Nussbaumer | ............. | 604/331 |
| 4,747,166 A | 5/1988 | Kuntz | | |
| 4,820,291 A * | 4/1989 | Terauchi et al. | ............. | 604/349 |
| 4,886,508 A * | 12/1989 | Washington | ............. | 604/327 |
| 4,957,487 A * | 9/1990 | Gerow | ............. | 604/133 |
| 5,002,541 A * | 3/1991 | Conkling et al. | ........... | 604/319 |
| 5,267,989 A | 12/1993 | Moyet-Ortiz | | |
| 5,267,990 A | 12/1993 | Cross et al. | | |
| 5,678,564 A * | 10/1997 | Lawrence et al. | ......... | 600/574 |
| 5,681,297 A * | 10/1997 | Hashimoto et al. | ........ | 604/355 |
| 5,792,132 A * | 8/1998 | Garcia | ................. | 604/385.01 |
| 5,911,222 A * | 6/1999 | Lawrence et al. | ......... | 600/574 |
| 6,186,990 B1 | 2/2001 | Chen et al. | | |
| 6,296,627 B1 | 10/2001 | Edwards | | |
| 6,311,339 B1 | 11/2001 | Kraus | | |
| 6,394,988 B1 * | 5/2002 | Hashimoto | ................. | 604/355 |
| 6,443,939 B1 * | 9/2002 | Oki et al. | ................... | 604/393 |
| 6,450,995 B1 | 9/2002 | Prabhakar | | |
| 6,554,817 B1 * | 4/2003 | Oki et al. | ................... | 604/393 |
| 6,592,560 B1 * | 7/2003 | Snyder | ...................... | 604/331 |
| 6,641,567 B1 * | 11/2003 | Williams | ................... | 604/327 |
| 6,652,481 B1 * | 11/2003 | Brown et al. | ................ | 604/35 |

(Continued)

OTHER PUBLICATIONS

"The 2001 Medical Design Excellence Awards" presented by Canon Communications LLC, 2000 Canon Communications LLC.*

(Continued)

*Primary Examiner*—Tatyana Zalukaeva
*Assistant Examiner*—Michael G. Bogart
(74) *Attorney, Agent, or Firm*—Robert Platt Bell

(57) ABSTRACT

VARS (Vacuum Assisted Relief System) is a aircrew bladder relief system that allows the pilot, whether male or female, to urinate in flight with comfort and convenience. There are three principle parts to the system, The pump, the garment, and the receiver. A pump and battery pack may be mounted in a breast pocket or attached to a torso harness at breast level. Locating the pump at a level higher than the garment insures little or no "leak back" to the garment. A garment worn like a diaper or underwear, includes an intake manifold comprised of a number of perforated tubes sandwiched between layers of material. Urine from a user is collected in the garment, drawn into the manifold tubes through these holes, by means of vacuum from the pump. Collected urine then passes through a hose into containment bag or receiver.

22 Claims, 9 Drawing Sheets

U.S. PATENT DOCUMENTS

| | | | |
|---|---|---|---|
| 6,706,027 B1* | 3/2004 | Harvie | 604/347 |
| 6,716,181 B1* | 4/2004 | Spencer et al. | 600/574 |
| 6,740,066 B1* | 5/2004 | Wolff et al. | 604/319 |
| 2001/0037098 A1* | 11/2001 | Snyder | 604/331 |
| 2003/0055388 A1* | 3/2003 | Clinton et al. | 604/353 |
| 2003/0150050 A1* | 8/2003 | Tanaka et al. | 4/144.3 |

OTHER PUBLICATIONS

"Infant Diapers and Incontinence Products: Choices for Families and Communities", Sherri A. Gahring, Thomas R. Halbach, and Wanda W. Olson, ©2002, Regents of the University of Minnesota, http:://www.extension.umn.edu/distribution/familydevelopment/DE5960.html.

"Function and Construction of AHPs", Dec. 9, 2002, Edana: Absorbants Hygiene Products, http://www.edana.org/uk/hygieneabsorbants/functions_ahps.html.

"Fibervisions", website, Dec. 9, 2002, http://www.fibervisions.dk/OurCompany.htm.

"Little John Portable Urinals at Aces Pilot Shop", Dec. 10, 2002, http://www.acespilotshop/pilot-supplies/safety/little-john.htm.

"Restop 1 Disposable Travel Toilet at Aces Pilot Shop", Dec. 10, 2002, http://www.acespilotshop.com/pilot-supplies/safety/rest-stop-1.htm.

* cited by examiner

VACUUM ASSISTED RELIEF SYSTEM (VARS)

FIELD OF THE INVENTION

The present invention relates to relief system for containing and removing urine or other human (or animal) waste from the body. In particular, the present invention is directed toward an undergarment provided with a vacuum pump for removing urine and the like from a human or animal. The present invention may also be used to drain wounds and the like.

BACKGROUND OF THE INVENTION

In general aviation (GA) and military aviation it is often not practical to provide restroom facilities on an aircraft due to weight, space, and cost concerns. Pilots and passengers in GA and military aircraft may be subjected to long flying legs or missions without the availability of restroom breaks. If a pilot or passenger has to urinate, it can be a distracting and dangerous condition, as it diverts attention away from flying the aircraft. Moreover, needs exist in other arts to provide devices for absorbing urine from children, incontinent adults, animals, hospital patients, and the like.

Adult diapers, catheters, and other urine collection devices are known in the art for absorbing or collecting urine from humans and animals. These various devices suffer from a number of drawbacks as is known in the art.

So-called adult diapers and the like are known for use with incontinent humans. Similar devices have been used with animals and the like. All are based upon infant diaper technology which uses absorption characteristics of various materials to wick away urine from the body. While the amount of research and development in this field has been considerable, and significant improvements have been made, these devices suffer from a number of drawbacks.

While babysitting his first grandchild in 1956, one Procter & Gamble (P&G) chemical engineer was determined to find a better way to diaper. He led a P&G group to research the possibilities of a disposable diaper that was absorbent, which prevented leaks while keeping babies dry ("Pampers Products", 2000).

Although the first alternative to cloth diapers was imported from Sweden by Johnson & Johnson in the 1940s, that product was marketed mainly as a convenience for traveling families. It was Pampers, introduced in 1961 as a result from the P&G research, which removed the diaper container and laundry delivery truck in most American households by the end of the 1960s.

Ever since, P&G and its main competitor, Kimberly-Clark (maker of Huggies), along with other smaller diaper manufacturers have engaged in an active competition in diaper marketing and technology for a $3.5 billion annual market. The second revolutionary breakthrough in diapering came in the late 1970s.

Commercial production of superabsorbent polymers began in Japan in 1978, for use in feminine napkins. This early superabsorbent was a crosslinked starch-g-polyacrylate. Polyacrylic acids eventually replaced earlier superabsorbents, and is the primary polymer employed for superabsorbent polymers today. In 1980 European countries further developed the superabsorbent polymer for use in baby diapers.

The first diapers employing this technology used only a small amount of polymer, approximately 1–2 grams. In 1983, a thinner diaper using 4–5 grams of polymer and less fluff was marketed in Japan. The use of superabsorbent polymers revolutionized the diaper industry.

Diaper manufacturers began to design diapers to take advantage of the amazing liquid retention ability of the polymer. Superabsorbent polymers absorb, and retain under a slight mechanical pressure, about 30 times their weight in urine. The swollen gel holds the liquid in a solid, rubbery state and prevents the liquid from leaking onto the baby's skin and clothing.

Despite advances in absorption material technology, the wicking action of such absorbants is not always perfect. As a result, excreted urine may still remain in contact with the skin of the user, causing rash or other difficulties. While improved diaper materials tend to do a good job of keeping infants dry, these materials may not perform well with adults, particularly when sitting down, as the pressure from the body tends to force the absorbed urine to the surface. Thus, even with advanced superabsorbant materials and the like, diaper technology still has drawbacks which make it unacceptable for adult use, particularly in aviation.

Presently there is no single device acceptable for use by both male and female aviators for bladder relief. Existing aircraft relief tubes do not currently provide the desired compatibility and practicability for use either by female or male. Unisex type interfaces do not conform well in either case. The present urine collection life support equipment is not able to meet the demands of the aircrew and can potentially lead to compromised flight safety, through distractions from connections and disconnections.

Female options are either a commercially available adult diaper or an oval-shaped funnel, which requires them to partially undress before use. Males have the external condom catheter, which can cause skin irritation from residual urine exposure. The most commonly used male urine collection device is the "piddle-pack", which requires the pilot to partially undress, loosen the lap-belt, extend the legs and often initiate a shallow dive to allow for use of the device.

Because of the problems associated with the present systems, many aircrews elect to self induce dehydration prior to a sortie to avoid the issue all together. Furthermore, there is no provision for use in aircraft where negative and positive "G" loading occurs. High-g maneuvers usually assure that the aircrew will have wet clothing from use and/or leakage from the storage container ("piddle-pack" for males and diaper for females). Long-term exposure to urine causes skin irritation and the possible development of shingles, which may render a pilot/aircrew member useless for days at a time.

Catheters and other invasive devices are also known in the art for collecting urine. Medical catheters require insertion into the urinary tract, a task which may be painful, and require a nurse, doctor or technician to perform. In addition to the risk of urinary tract infection, such catheters may be uncomfortable if used for an extended period of time.

Other types of urine collection devices have also been sold to motorist and general aviation users. These devices which may be sold under the trade name LITTLE JOHN™ (See: http://www.acespilotshop.com/pilot-supplies/safety/little-john.htm incorporated herein by reference) are little more than containers provided with screw or snap-on adapters for male and female body parts. These devices require the use of gravity in order to make them work, and also require partial undressing of the user, which may be impractical in a small aircraft. In addition, these devices may not seal properly, and require the user to manually remove the device from storage, use it, and return it carefully to storage. Such devices, being open in use, may create odor problems as well.

Another product marketed to General Aviation users and the general public is sold under the trade name RESTOP® 1 (See: http://www.acespilotshop.com/pilot-supplies/safety/rest-stop-1.htm incorporated herein by reference). Chen, U.S. Pat. No. 6,186,990, issued Feb. 13, 2001, and incorporated herein by reference, discloses a similar product. This solution provides a container filled with an absorbent gel. When a user urinates into the container, the urine is absorbed into the gel and allegedly rendered odorless, harmless, and easy to handle. Of course, this solution is 100% disposable, and like the LITTLE JOHN™ requires the user partially undress to use.

In the medical, aviation, and aerospace arts, various other urine collection devices are known. Some such devices are similar to a catheter except that in place of a tube which is inserted into the urinary tract, a rubber or elastic cup-like device with an attached collection tube is attached to the male penis. Examples of such devices may be found, for example, in Moyet-Ortiz, U.S. Pat. No. 5,267,989, issued Dec. 7, 1993 and Cross et al., U.S. Pat. No. 5,267,990, issued Dec. 7, 1993, both of which are incorporated herein by reference. Such devices can also cause discomfort and irritation, and also may not be adaptable to female pilots. Like catheters, such devices cause unnecessary irritation when the user does not need to urinate.

Additionally, an important aspect of any relief system is the ability to relax to be able to use the device. This is very important as urination begins from a relaxation process not contraction process. A good relief system will have wide social acceptance whether it be for an astronaut, wheelchair victim, emergency vehicle driver, long distance cyclist, triathlete, glider pilot, recreational pilot, bed-ridden patient, incontinence, or someone with other bladder problems.

A new solution is needed to resolve the problems of leakage in adverse aircraft orientation and also address the issues of fit and comfort. The new system should not inhibit the use of ejection seats. The new solution should include a full-dress hands-free operation. The new solution should be easy to put on, comfortable to wear, and easy to remove. Leakage should be eliminated. It should also be compatible with current aircrew protective assemblies such as the Advanced Technology Anti-G Suit (ATAGS). The new solution should share commonality between the male and female systems. A single comfortable device is a necessity.

Thus, a need exists in the art for a system which may be comfortably worn by pilots and passengers of both genders (as well as hospital patients, the incontinent, and animals), which will collect and remove urine away from the body without irritating the skin or creating discomfort.

SUMMARY OF THE INVENTION

VARS (Vacuum Assisted Relief System) is an aircrew bladder relief system that allows the pilot, whether male or female, to urinate in flight with comfort and convenience. There are three principle parts to the system, The pump, the garment, and the receiver.

A pump and battery pack may be mounted in a breast pocket or may be attached to a torso harness, which may be at breast level. Locating the pump at a level higher than the garment may insure that little or no "leak back" occurs to the garment. The garment may be worn like a diaper or underwear, and may include an intake manifold comprised of a number of perforated tubes sandwiched between layers of material. Urine from a user may be collected in the garment and drawn into the manifold tubes through these holes, by means of vacuum from the pump. Collected urine then passes through a hose into containment bag or receiver.

Comfort for long flights is achieved through a natural interface. The system is attached to the body by belt clip, pocket, or other methods. The system includes barrier creams, an interface that replaces existing undergarments, plastic tubing, pumps, and reservoirs. The system has features that provide for hands free operation and essentially eliminates leakage and drying of the skin. This system has usage across the social spectrum, from astronauts to those confined to wheelchairs.

DETAILED DESCRIPTION OF THE INVENTION

Figure 1:
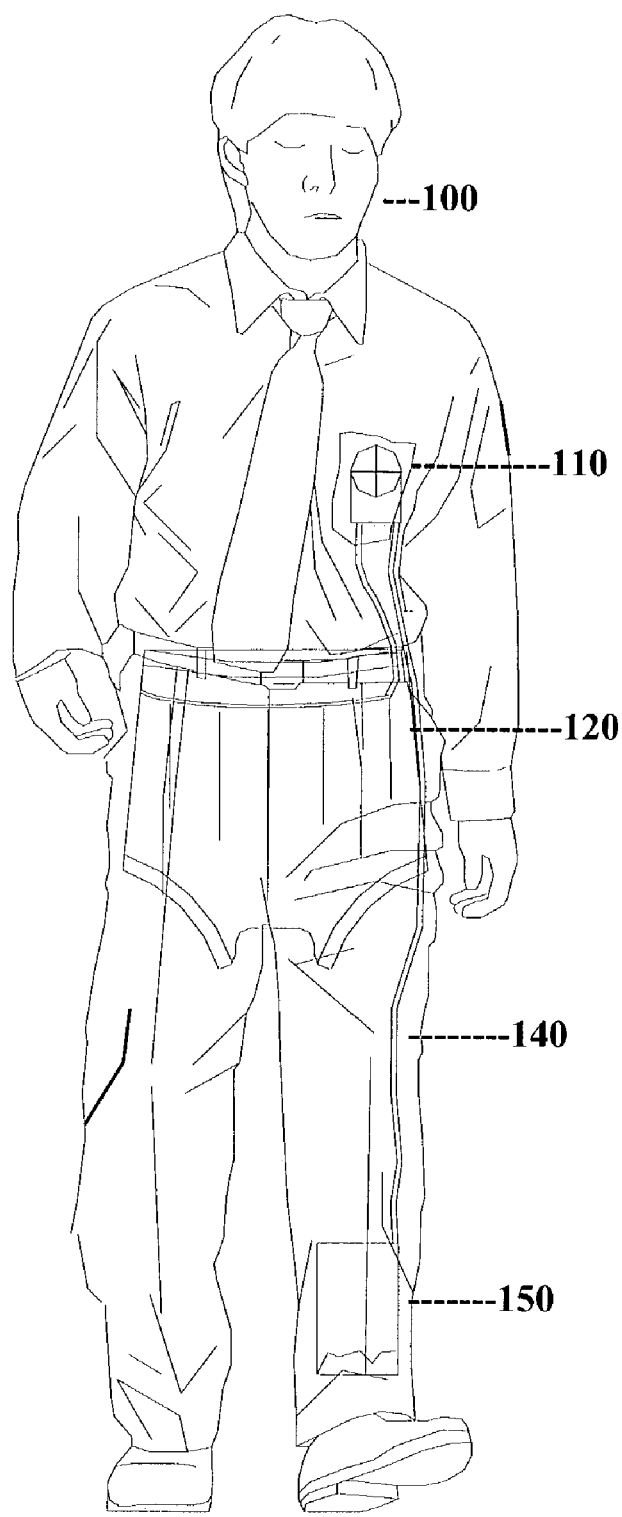
FIG. 1 is a perspective exposed view of the apparatus of the present invention as mounted on a user.

FIG. 1 is a perspective exposed view of the apparatus of the present invention as mounted on a user 100. In this civilian embodiment, pump and battery pack 110 is illustrated mounted in a breast pocket or attached to a torso harness at breast level. Locating the pump at a level higher than the garment insures little or no "leak back" to the garment.

Figure 2:
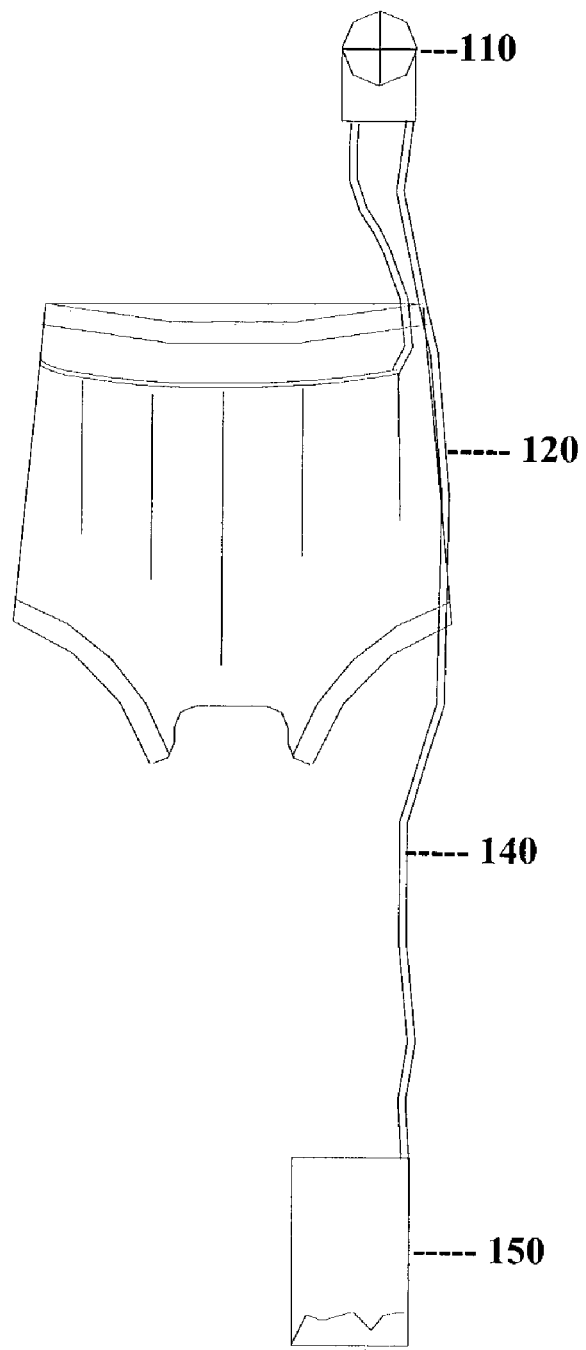
FIG. 2 is a perspective front view of the components of FIG. 1.

Garment 120, as will be described in more detail below, includes an intake manifold comprised of a number of perforated tubes sandwiched between layers of material. Urine from user 100 is collected in the garment, drawn into the manifold tubes through these holes, by means of vacuum from pump 110. Collected urine then passes through hose 140 into containment bag or receiver 150. FIG. 2 is a perspective front view of the components of FIG. 1.

In a military application, the apparatus may be partially mounted to a survival vest such as a P/N LPU-10/P MIL-38484 United States Air Force (USAF) and pump/battery pack 110 may be installed in the upper left pocket directly behind the knife pocket. Hoses 130 may be routed through small holes in the bottom of that same pocket. A control switch (not shown) may be located on the front side of the knife pocket. Receiver 150 is normally mounted to the ankle.

The present invention may be provided in two basic embodiments. In a first embodiment, the system may be mounted on the body. In a second embodiment, part of the system (pump, tubing, receiver) may be installed to an aircraft or other vehicle (or otherwise mounted externally). Although disclosed herein as primarily directed toward aircraft applications, the system of the present invention may also be applied to other vehicles, both military (e.g., tank, HUMVEE, armored personnel carrier, or the like) or civilian (car, truck, wheelchair, motorhome, or the like) In addition, the apparatus of the present invention may be applicable in marine applications where a user cannot easily get up to use a restroom (e.g., boat pilot) and may be used in both military and civilian applications.

The present invention may have applications for spacecraft as well. By providing a standardized design for both men and women, with a non-invasive body interface, the present invention is an improvement over prior techniques used with astronauts and the like. In addition, the present invention may be useful for the incontinent, those in nursing homes, hospitals, and the like, as it may require less frequent diaper changes and the like and provide greater comfort than other Prior Art techniques such as catheters, diapers, and the like, In the preferred embodiment, particularly for aircraft applications, the unit may be completely mounted to the body of the user, and the battery/pump unit may be mounted in an existing pocket of the survival vest or a new pocket added to the vest for this purpose. This is also important to relieve the concerns about entanglement during ejection and also to make the product more readily adaptable to civil applications and achieve commercialization.

For other applications, such as hospitals and the like, portions of the apparatus may be mounted externally to make emptying the receiver easier. Moreover, in such an embodiment, a battery pack may be externally mounted or may be supplanted or charged by a power supply from a wall-pack transformer (e.g., hospital or home application) or from 12 VDC socket (e.g., automotive or GA application).

Figure 3A:
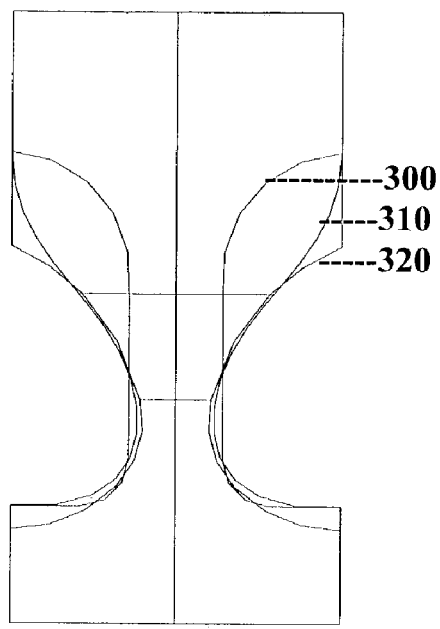
FIG. 3A is a plan view illustrating the superposition of male and female diaper patterns superimposed over one another, wherein the bottom of the Figure represents the front portion of the garment patterns.
Figure 3B:
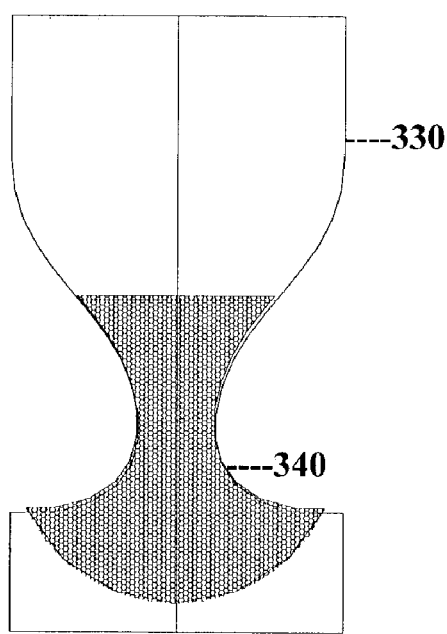
FIG. 3B is a plan view a resultant unisex garment design for use in the present invention, where the bottom of the Figure represents the front of the garment.

FIG. 3A is a plan view illustrating the superposition of a male diaper pattern 300 and a female diaper pattern 310 superimposed over one another, where the bottom of the drawing represents the front portion of the garment patterns. FIG. 3B is a plan view of a resultant unisex garment design 330 for use in the present invention, where the bottom portion of the drawing represents the front part of the garment. The drawings of the male/female designs 300, 310 were superimposed over the top of each other as illustrated in FIG. 3A to determine a possible shape of a uni-sex garment 320 pattern. The initial layout for the manifold 340 on resultant garment 330 is illustrated in FIG. 3B.

Figure 4:
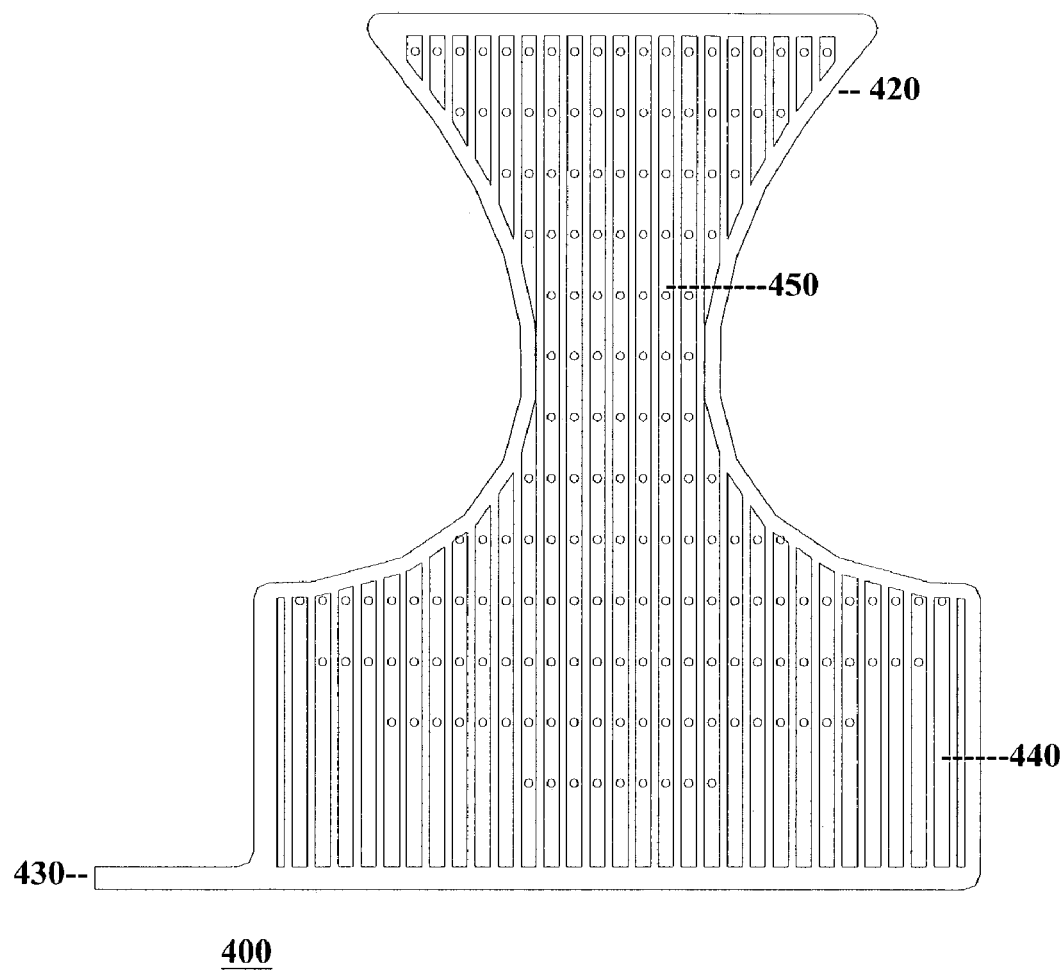
FIG. 4 is a plan view of the inlet manifold of a first embodiment of the present invention.

FIG. 4 is a plan view of the inlet manifold 400 of a first embodiment of the present invention. Manifold 400 comprises a number of tubes 440 provided with inlet holes 450 coupled together with a collector tube or tubes 420. Since manifold 400 may pass through a narrow region in the center, some of tubes 440 might not be routed directly through the center. Thus, a slightly larger collector tube 420 may be used at the extremities to act as a collector manifold to provide access to all regions and provide better surface coverage of the center area.

In an initial embodiment, a total of 29 tubes 440 of 0.18751" OD and 0.1251" ID were provided in manifold 400, running longitudinally in the garment as illustrated in FIG. 4. Seven of tubes 440 run directly down the middle. These tubes may be 13.625" in length. The remaining 22 of tubes 440 have varying lengths with an average length of 3.85". All 29 of tubes 440 should reach the collector tubing 420 around the perimeter of manifold 400. An outlet tube 430 may be connected to the urine collection device and vacuum pump as illustrated in FIGS. 1–2 discussed previously.

The perimeter collector tubes 420 may be 0.25" OD and 0.18751" ID. The 29 center tubes 440 may have approximately 180 holes 450 in 1" increments which perforate one side of tubes 440. Each hole 450 may measure 0.125" in diameter.

During voiding, urine may access only about 30% of the surface area of manifold 400. In other words, about 54 of these holes 450 may typically be used for drainage for either male or female users. To test this design, a solid model of this was generated in AutoCAD for Computational Fluid Dynamics (CFD) studies to verify operation of the apparatus.

In locating the receiver, the estimated maximum height the receiver will be above the garment is 36 inches. As a result of the confines of an aircraft, in an aircraft installed embodiment, this may be a worst case scenario. When the receiver is mounted lower, the situation improves. The desired tube diameter may be 0.25" ID or smaller and may need to be varied depending upon application. Through experimentation the present inventor has discovered that the number of tubes running through the garment could be greatly reduced. In a revised embodiment, only two tubes may be necessary to run through the garment which connects to the tubing around the waist.

Figure 5:
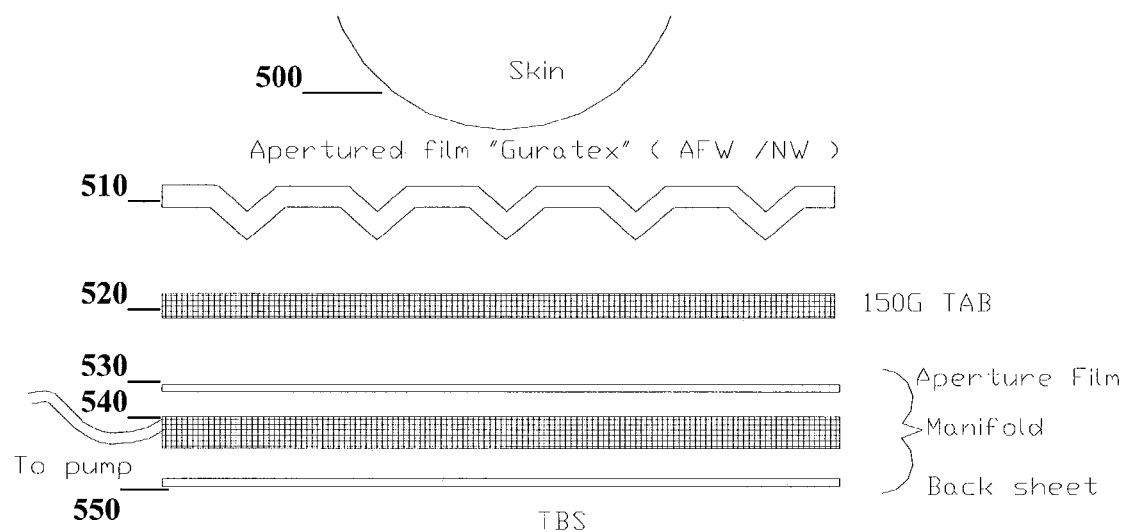
FIG. 5 is a cross-section view of the garment of the first embodiment of the present invention.

FIG. 5 is a cross-section view of the garment of the first embodiment of the present invention. The garment may have multiple layers of material with the manifold imbedded in between these layers. The production process may be similar to diaper production. The method of production may need to be modified slightly in order to imbed the manifold in the garment. For example, the manifold may be held and released from a production drum with a timed vacuum source.

In the present invention, fabric selection was determined after a careful research and consultation with various experts in the undergarment fabric industry. Skin 500 may come in contact with first layer 510. First layer 510 may be formed of Guratex™, which is an aperture film with a non-woven scrim (AFW/NW) layer attached. Aperture film has small holes in it the shape of a funnel, which helps to move fluid in only one direction. When first layer 510 is magnified it can be seen that there are non-woven fibers passing over the holes of the aperture film. Proper orientation of this film is important such that the apertures point away from the body, allowing fluid to pass into the lower layers, but not to return.

Second layer 520 may comprise a through air bonded (TAB) material which allows nesting of the apertures and the spreading of fluids to the manifold. Second layer 520 may be made from one to three plies of material. The through air bonded TAB 10 gram is a material similar to bleeder/breather that is used in the composite industry.

Third layer 530, an aperture film, is the start of the manifold. A porcupine type roller may be used to form the aperture film for forming the number of holes, or such holes may be punched or otherwise machine formed. The number of holes may be varied to determine optimum performance of the apparatus.

Fourth layer 540 forms the center of the manifold and may comprise either TAB or bleeder/breather, a polyester non-woven fabric. The density of material may be increased around the tube exit area. In any event, the manifold nests in this material. Fifth layer 550, an outside layer back sheet (TBS) may comprise a treated breathable sheet or breathable polyethylene (PE) film.

By using the materials discussed above, (in connection with FIG. 5), the edges of the apparatus may be sealed together by heat bonding, melting adhesive (e.g., hot glue), air stitch, or other methods. Such garment construction lends itself to inexpensive mass production.

Prior to using the garment, a barrier cream such as Gloves in a Bottle™ (Gloves In a Bottle, Inc., 3436 North Verdugo Road, Suite 100, Glendale, Calif. 91208, www.glovesinabottle.com) may be applied to the skin. Application of this thin film reduces the natural oil and moisture loss, protects the skin and allows the skin to heal itself. Gloves in a Bottle™ (Formula Identification Number 324986) helps the outer layer of skin to keep its natural oils and moisturizers that protect the deeper layers of skin, leaving the skin soft and supple. This type of product assists the outer layer of skin functioning so well so it can breathe and perspire naturally. According to the manufacturers, Gloves In A Bottle™ becomes part of the outer layer of skin itself, it cannot be washed off like conventional lotions. It comes off naturally with exfoliating skin cells.

Figure 6A:
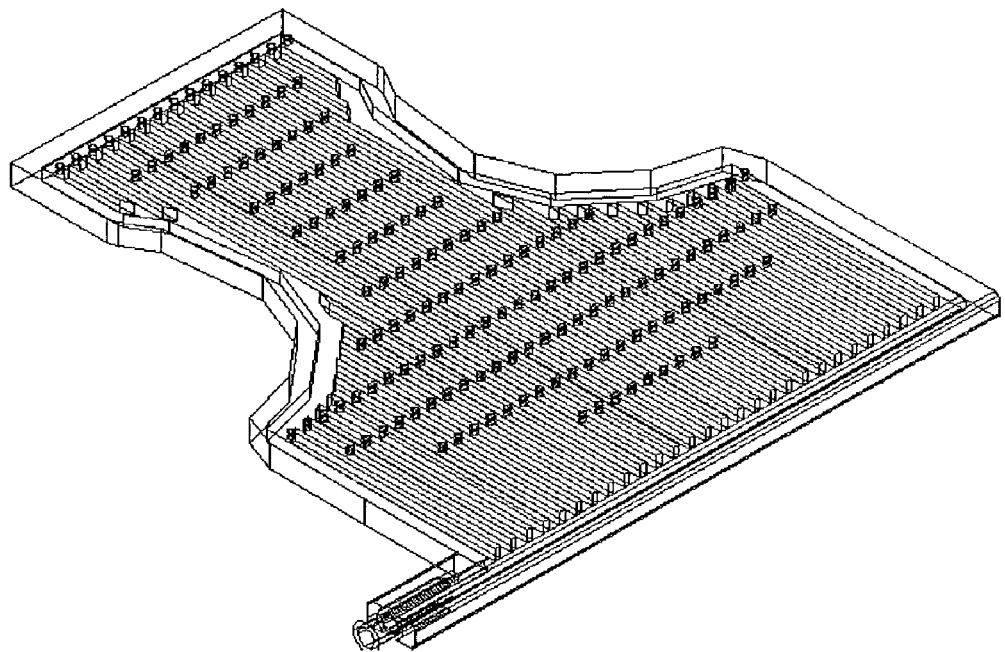
FIG. 6A is an exposed CAD model of the manifold of the present invention.
Figure 6B:
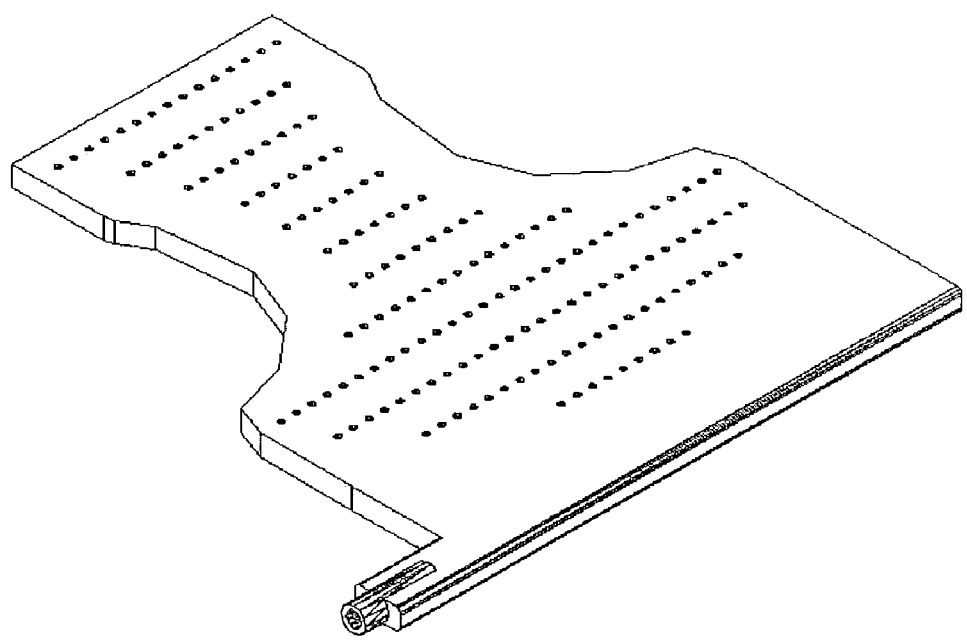
FIG. 6B is an exterior view CAD model of the present invention.

FIG. 6A is an exposed Computer Aided Design (CAD) model of the manifold of the present invention. FIG. 6B is an exterior view CAD model of the present invention. Both FIGS. 6A and 6B were prepared in AutoCAD. Separate Computational Fluid Dynamics (CFD) runs were prepared for female and male to compare patterns or urine flow. These CFD runs confirmed the proper operation of the device and helped illustrate flow patterns.

Extensive research has been done to determine a suitable pump/motor combination in the hopes of finding a pump motor combination which meets all requirements of the present invention and could be purchased as an off the shelf item. Due to the fact the pump is sometimes pumping fluid and sometimes pumping air it was determined that the pump sizing should be done experimentally. In order to meet all of these stringent requirements, it may be necessary to purchase the pump from one manufacturer and the motor from another, combining these units in custom enclosure.

Some of the stringent requirements the pump should handle are as follows. The usual range of fluid quantity voided per occasion is approximately 2 to 400 CC (i.e., 0.002 to 0.42 quart). For a conservative design it is desired for the system to be designed for at least one quart capacity over a 30 second interval. In addition, there is a practical limit on the pump size based on battery life, physical size, and the amount of vacuum, which can be applied to sensitive areas. For initial calculations, the pump was designed to operate at 90% capacity; with the ability to pump 32 ounces in a minute or less. Flow may be unsteady, as only 30% of the holes in the manifold may have contact with urine.

Peristalsis is one of the oldest pump designs. Early Greeks used the word peristalsis to describe the operation of a wave of automatic contractions, propelling contents along body tubes to transport food and body waste. Simply substituting with thermoplastic tube and rollers for contraction and we have the peristaltic pump.

By mechanical simulation the tube walls are squeezed together to form a seal as the roller moves along the tube. The previously compressed tube regains original form and sucks fluid/gas into the formed vacuum to create a self-priming function. The fluid/gas will follow the rollers until the tube is no longer compressed and by this time a 2nd or even 3rd roller is compressing the tube, preventing back flow and pushing the initial dose of fluid/gas out of the pump. By a repetitive operation as the rollers rotate we are creating a pumping movement, which has an element of pulsing as a standard. By the squeezing of the tube the rotor creates suction lift and outlet pressure.

Peristaltic pumps operate with the roller and tube assembly creating a movement of liquid through 180 degrees. Other forms of peristalsis would create this movement through 120 degrees but generally in such instances the flow volume is much reduced. In the preferred embodiment, a pump in the 100 ml range capable of sustaining a vacuum of at least 2 psi is used. However with improvements in efficiency in pumps and manifold designs (e.g., fewer holes) less vacuum may be used.

Better performance is achieved using a pump capable of 7–10 psi. The pump should be self-priming and capable of handing liquid and gas. Pump P/N 909-282-12VDC manufactured by ANKO (3007 29th Avenue East, Bradenton, Fla. 34208) suitably modified for pocket use, forms a part of the preferred embodiment of the present invention.

The MityFlex 909 Series pump by Anko Products is capable of pumping from 3 mL/minute to over 987 mL/minute. It runs on 12 VDC, and can operate at 40 fixed flow rates. The pump is approximately 5.12"W×3.74"H× 4.55"D and uses a DC gearmotor with a stainless steel output shaft. The pump can operate at pressures up to 20 psi (2.7 bar). This pump fits the guidelines for the present invention with the exception of overall depth. However, the present inventors have found that the pump housing may be modified without detracting from performance of the pump in order to achieve a desirable thickness. With the gearbox reversed and the motor feeding power to the opposite side of the gearbox, and the mounting plate removed, the motor thickness can be considerably reduced. The batteries may be nested around the motor to provide a compact pump/battery package.

The Anko pump uses 3.2 amperes during continuous operation. Batteries are rated in Amp hour ratings. For example, a 5 Amp hour battery will operate at 5 Amps for one hour or 2.5 Amps for 2 hours. The present system has a design goal of operating for two minutes, twice an hour, for 8 hours. Thus the battery requirements are 4/60×3.2× 8=1.706 Amp Hours. Small batteries are rated in the milli-Amp-hour range, so the minimum battery required for this design would be approximately 1700 mA Hours.

There are several types of batteries categorized by their ability to be disposable or rechargeable and further by their chemical construction. To achieve the required voltage, battery cells may be connected in series. The voltage available from each cell falls in a range of 1.2 to 3.6 volts per cell. For the present invention, a Lithium Ion battery was selected as it produces the highest volt per cell or energy density. So instead of connecting ten 1.2 Volt cells to generate the require 12 Volts, only four cells are required, which reduces packaging requirements.

Of course, other types of pumps and voltage requirements may be used without departing from the spirit and scope of the present invention. A lower voltage pump, for example, could be used (e.g., 6 Volts) or one operating at a higher voltage (e.g., 24 Volts). Similarly, other types of batteries and pumps may be used without departing from the spirit and scope of the present invention.

The pump/motor/battery pack may be enclosed in a single enclosure small enough to fit in the pocket of a survival vest or the like. The case may be made of high impact plastic using resin transfer method. This plastic has short filaments of fiberglass imbedded in the resin, allowing the part to be strong. It may be manufacturable at high levels of production, thus reducing cost.

Consideration should be given regarding the delivery pressure required from a peristaltic pump, as most peristaltic pumps operate with a delivery pressure of less than 15 PSIG unless some form of exceptionally thick wall or reinforced tubing is used. There are many good reasons to use the peristaltic pump, including its quiet operation for commercial applications.

In the present invention, concerns about corrosion from the caustic environment is eliminated as no internal part of a peristaltic pump comes in contact with the fluid. These units are low cost at an OEM level. Mostly they can be made compact which is ideal for the present invention.

Most Peristaltic pumps are used for small volumes of fluid, as an example its most common use is in the medical field where small dosages of medicines are dispensed at low dosages. The pump used in the present invention should a have a relatively high flow rate and be self-priming. There are some other requirements as well it should be low weight and energy efficient in order to use batteries for its operation.

The pump may handle both fluid and air. Positive displacement pumps are best suited for use where the process needs to be versatile and the substances entering the pump vary. The positive displacement pumps are normally self-priming and can handle gaseous products. However, most positive displacement pumps require pressure relief systems to prevent damage to the pump or system if a valve is closed or the outlet blocked.

Two other types of pumps that may be used in the present invention are also positive displacement pumps. The types of positive displacement pumps that may be suitable to the aircrew relief system are the diaphragm pump and the flexible impeller pump. The diaphragm pump pulses one or two flexible diaphragms to gently displace liquid using check valves to control the direction of the fluid flow. The diaphragm pump weighs approximately 5.5 pounds and measures 9⅜" by 3⅞" by 6".

The flexible impeller pump is a low-cost utility pump that contains an impeller that traps fluid between the blades and sweeps it through the pump housing. The flexible impeller pump is ideal for general transfer applications. This pump weighs approximately 4.3 lbs and measures 6"×4"×3" (L×W×H). Both types of pumps are available commercially in a field-portable 12 Volt DC versions.

Shape memory alloys, such as Nitnol, may be combined with a diaphragm type pump to create a pump that would produce a noiseless vacuum and be lightweight and energy efficient. Shape memory alloys are lightweight materials which are able to shrink in the 6% range when heated at low voltages.

For experimental testing, a layout was determined for the test equipment and test stand. During fabrication, an additional vacuum gauge was needed in order to measure any pressure drop in the system. For initial testing, article sheets for all tests were 8.5"×11" sheets.

Testing started with an outside sheet of PE film and followed by a sheet of 4.5 oz bleeder/breather with only the end wrapped around a simple manifold tube. The manifold tube consisted of a 6" length of tubing with a total of (8) ⅛" holes in the side. The aperture film was formed in-house using a porcupine roller to produce approximately 1200–1300 holes in the sheet. A sheet of PE film was used to simulate the skin contact.

These test sheets were placed on the mannequin to simulate the shape of the garment. The test rig was changed in several ways to make testing simpler and more accurate. First a flow meter was added to determine pump capacity. This required two iterations to achieve proper sizing. A funnel that contains a valve was added so that the measured fluid could be introduced in an accurate fashion. This required an increase in working height to prevent fluid from trapping in the hose during introduction.

During testing, it was discovered that some water was able to get by the water separator so a second trap was added to recover this fluid. An electronic scale was added to record before and after samples. By using two pressure gauges on either side of the water separator, it was determined experimentally that there is about 1 PSI pressure drop through the water separator.

A typical test may proceed as follows. First, the vacuum pump is started and allowed to stabilize. This typically takes about 2 minutes before the test can begin. The control valve is closed until the desired pressure is achieved. 60 grams of water are then placed in the hopper with the valve closed. Opening the valve of the hopper starts a test. When water starts to enter the aperture film an immediate increase in vacuum is noticed. This value is recorded.

Next, comparing a mark placed on the trap to indicate when 40 grams of fluid have transferred, this value is recorded in seconds elapsed from the start. The test continues until two minutes have passed and all tests are terminated. With the system shut down fluid is drained from the traps and measured using the electronic scales. The values are recorded and the next test is prepared. Just prior to discontinuing testing you can still observe some fluid traveling in the hoses but its level of transfer is low at least so far.

The test results found that values of pressure below 2 PSI will cause slow operation and possible unsatisfactory results. However, with improved manifold designs (e.g., fewer holes), less vacuum may be acceptable. Values greater than 3 PSI show near same performance with regard to recovery of fluids but the time to recover fluid is improved with increasing pressure. Efficiency was determined as the ratio between the amount of fluid put into the garment and the amount pulled out. 40 grams was chosen as a marker to indicate when most of the fluid has transferred at this point the garment feels dry to the hand.

In a typical test as soon as the fluid contacts the garment, the fluid immediately begins to transfer. There were some sources of error in testing. There is some lag in time with each test due to the water passing from the funnel through the hoses to the garment. Some moisture collects in the tubing with each test that is difficult to account for. With higher pressure, the water separator is less efficient at separating the water out as some fluid is noted entering the flow meter.

For human testing, a sample article was made with materials that were known to work from previous lab tests with a test device used on a human arm. The test article sheets for all tests were 8.5"×11". Starting with an outside sheet of PE film and followed by a sheet of 4.5-oz bleeder/breather with only the end wrapped around a simple manifold tube. The manifold tube consisted of a 4" length of ¼" tubing with a total of (4) ⅛", holes in the side. The aperture film was formed in house using a porcupine roller to produce approximately 1200–1300 holes in the sheet.

The test article was placed on the arm of the principle Investigator (PI) and secured in place with rubber bands.

The hose which transfers the fluid was simply place under the edge of the article, allowing the fluid to flow in random directions. The bulk of the fluid will transfer in about 2 minutes. The article was then removed to inspect for residual fluid against the skin and article. Trace amounts of fluid were remaining on the skin and between the holes of the aperture film. Any remaining fluid would have dried with continued running of the pump.

The manifold undergarment has been worn for about a 4-hour period at a time before testing. Two manifold tubes were run parallel between the legs of the test garment. The tubes were found to be slightly uncomfortable between the legs, so the shapes of the tubing running between the legs will be changed to an hourglass shape to achieve greater comfort when wearing the garment. The desired results of removing the urine from the test undergarment were achieved. The undergarment was kept in place for another 2 hours then removed and dissembled for examination. Trace amounts of fluid remained in the core of the manifold. Any remaining fluid would have dried with continued running of the pump.

The most likely point of failure was the ability of the fluid to pass from the body to the garment to the pump. One interesting result of this testing was that it was determined that the fluid tends to act as a seal and improve the performance of the aperture films. In addition, the continued drying effect due to the airflow produced by the vacuum pump is also an important effect of the present invention discovered during testing.

Figure 7:
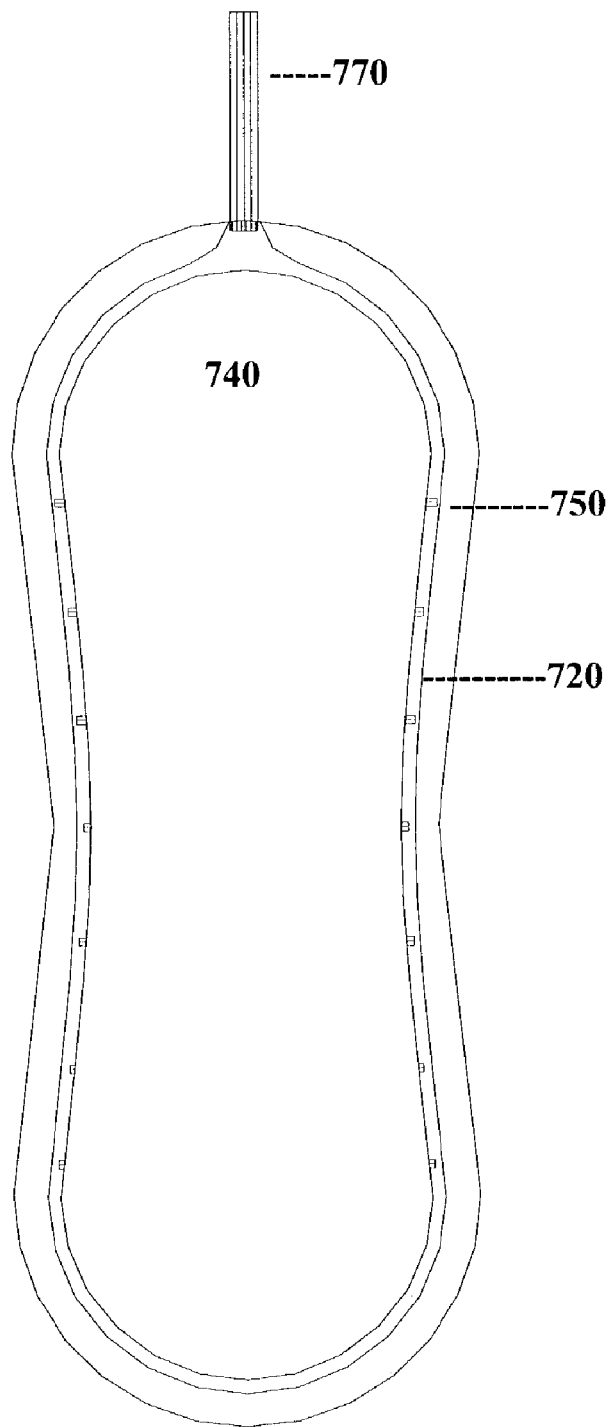
FIG. 7 is a plan view of the preferred shape of the garment of the present invention.
Figure 8:
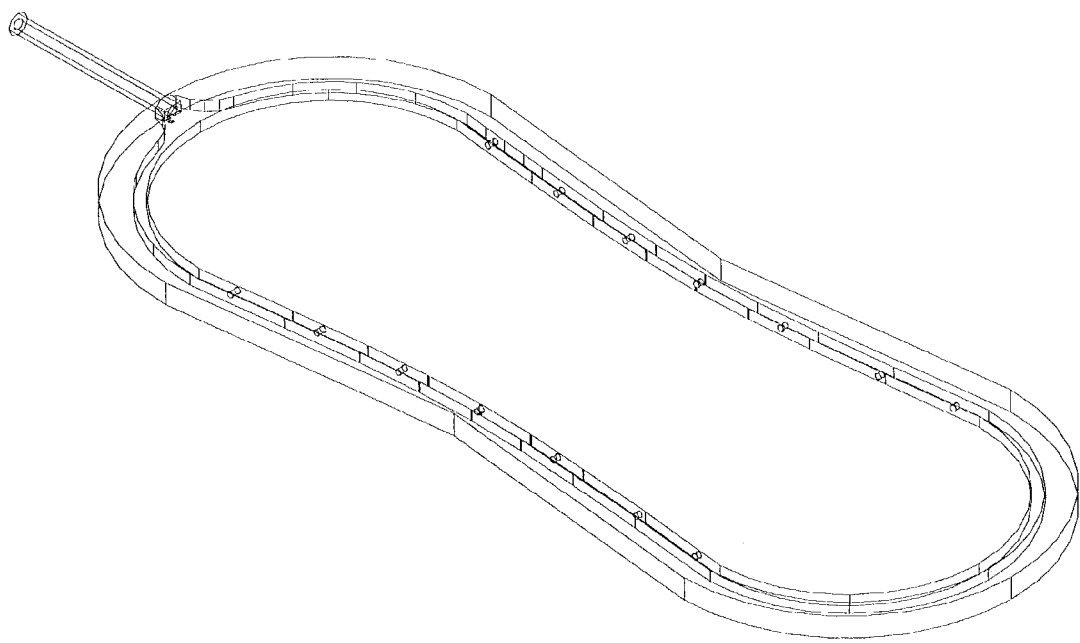
FIG. 8 is a perspective view of the apparatus of FIG. 7.
Figure 9:
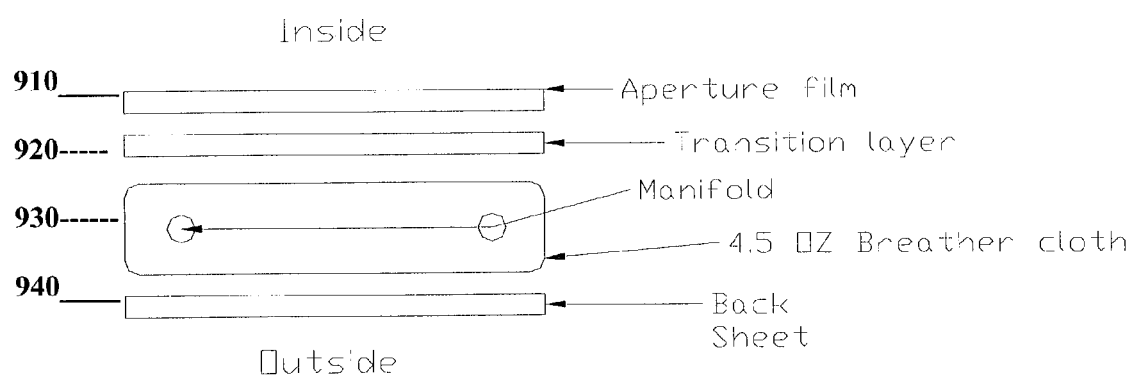
FIG. 9 is a cross-section view of this preferred embodiment of the present invention.

FIGS. 7–9 illustrate a preferred embodiment of the present invention. FIG. 7 is a plan view of the preferred shape of the garment of the present invention. FIG. 8 is a perspective view of the apparatus of FIG. 7. In this preferred embodiment, manifold 720 has evolved from a complex array of tubes to a single unit with only eight holes 750. This is an important improvement in reducing the cost of the unit and achieving manufacturability. Manifold 720 may comprise a loop as illustrated in FIG. 7, or may comprise a single tube or small number of tubes.

In the preferred embodiment, manifold 700 has tubes or cavities 720 running along the outside of the core 740 in an hour glass shape. Each of these tubes 720 has small holes 750 oriented toward the inside of the apparatus. Manifold 700 is constructed so that it is soft to the skin but rigid enough to prevent collapse of the tubes 720 during operation.

Tubes 720 may comprise Latex™ tubing with holes 750 approximately ⅛" in diameter punched along the inside. Tubes 720 in turn are connected to a T fitting 770 at the front which goes to the pump (not shown) in a similar manner to the first embodiment discussed above in connection with FIGS. 1–6. This type of construction lends itself to prototype development. During production this design may be fabricated from a corrugated plastic similar to that used in plastic sign construction.

FIG. 9 is a cross-section view of the garment of the preferred embodiment of the present invention. Tubes in manifold 930 may be nested into 4.5 oz bleeder/breather cloth (non woven polyester) otherwise known as TAB. The outside layer 940, known as a back sheet, may comprise a plastic film or coated nylon for a waterproof backing that is breathable. A transition layer 920 may be provided which allows the fluid to disperse and also prevents damage to the cones of the aperture film 910. The innermost layer is the aperture film 910 which acts as a one way check valve allowing fluids to come in but not back out. The orientation of the cones is pointed toward the manifold. Additional layers may be added to improve wearability and comfort.

In one version of the preferred embodiment, disposable protective underwear P/N PASPE630AA manufactured by Tyco/Healthcare/Kendall, 601 Allendale Road, King of Prussia, Pa. 19407, and distributed by Wal-Mart has been found to be more than suitable for use in the present invention. The absorbent core is simply removed from this off-the-shelf product and directly replaced with the vacuum core of FIGS. 7 and 8, secured with spray adhesive, and the product reassembled.

The Tyco protective underwear has features like elastic bands to seal the edges and high waste band which are well known to this field and comes as a uni-sex garment, making it more than suitable for use in the present invention. The small/medium size fits anywhere from 34" to 46" hips, making it applicable to a broad range of users.

The apparatus of the present invention may be activated in a number of ways. In the preferred embodiment, a timer or the like may be used to periodically activate the apparatus to remove any urine waste from the garment. In this manner, a simple, hands-free operation is assured. In an alternative embodiment, a manual switch may be provided to allow a user to manually evacuate the garment. A manual switch and timer may be used either alone or in combination. In another embodiment, which may be provided singularly, or in combination with the other activation means, a moisture sensor may be provided to allow the system to automatically activate when moisture is detected.

Other techniques for activating the present invention may also be used. For example, in an embodiment using vehicle power or the like, the apparatus may be left on all the time. As noted above, the vacuum pump tends to produce a pleasant cooling and drying effect in addition to voiding urine from the garment. In other applications, other sources of vacuum may be used. For example, for an airplane, the low pressure outside the aircraft, suitably regulated to prevent excessive vacuum, may be used to void urine from the garment. This vacuum may be used to collect the urine into a receiver or to direct the urine outside the aircraft.

While the preferred embodiment and various alternative embodiments of the invention have been disclosed and described in detail herein, it may be apparent to those skilled in the art that various changes in form and detail may be made therein without departing from the spirit and scope thereof.

For example, a ball check valve may be located between the pump and the receiver. The ball check valve may prevent accidental spillage during inverted maneuvers. A similar system is used in aircraft lead acid battery vents. Quick-connects may be added to the hoses to ensure proper connection by either male or female connectors or by using different sizes of fittings for different connectors.

In addition, the present invention may also be used to form a device that can be used by hospitals in what is currently called a dead pad. This pad is placed under the patient. Presently body fluids are passed into this article and absorbed in an absorbent core requiring regular replacement. Using the principles of VARS, these fluids could be removed allowing the patient to be more comfortable for longer periods of time. The present invention may also be used to obtain fluid samples (e.g., urine samples) for testing and analysis in a non-invasive manner. In addition, the present invention may also be used, in the same or modified form, to drain fluids from wounds and the like.

As noted above, the present invention may be made into a form suitable for use with animals other than humans, including research animals, zoo animals, farm animals, animals in transport, and the like. The apparatus of the present invention may be used, for example, with horses and the like to capture urine in situations where such animal urine may be objectionable (e.g., city environment or the like).

I claim:

1. A Vacuum Assisted Relief System for collecting animal fluid, said system comprising:
   a garment, worn by the animal and contacting at least a portion of the animal where fluid is generated, the garment including at least one hose coupled to the garment, for collecting fluid from the animal;
   a pump, coupled to the hose, for creating a vacuum on the hose to draw fluid from the garment and outputting the fluid from the pump; and
   a receiver, coupled to the pump, for receiving fluid output from the pump,
   wherein the garment comprises a diaper and the at least one hose includes a manifold tube provided with a plurality of holes in the manifold tube, for receiving fluid from the garment, and
   wherein the manifold tube comprises a manifold loop provided with a plurality of holes in the manifold loop, for receiving fluid from the garment.

2. The system of claim 1, wherein the diaper comprises a disposable diaper including a number of layers of material, and the manifold loop is sandwiched between layers of the disposable diaper.

3. The system of claim 1, wherein the pump comprises a peristaltic action pump creating a vacuum of at least 2 psi.

4. A Vacuum Assisted Relief System for collecting animal fluid, said system comprising:
   a garment, worn by the animal and contacting at least a portion of the animal where fluid is generated, the garment including at least one hose coupled to the garment, for collecting fluid from the animal;
   a pump, coupled to the hose, for creating a vacuum on the hose to draw fluid from the garment and outputting the fluid from the pump; and
   a receiver, coupled to the pump, for receiving fluid output from the pump,
   wherein the garment further includes a manifold comprising a plurality of tubes having a plurality of holes formed therein, the plurality of tubes being joined by at least one header to the hose such that fluid is collected in the plurality of holes and drawn into the hose.

5. A Vacuum Assisted Relief System for collecting animal fluid, said system comprising:
   a garment, worn by the animal and contacting at least a portion of the animal where fluid is generated, the garment including at least one hose coupled to the garment, for collecting fluid from the animal;
   a pump, coupled to the hose, for creating a vacuum on the hose to draw fluid from the garment and outputting the fluid from the pump; and
   a receiver, coupled to the pump, for receiving fluid output from the pump,
   wherein the animal is a human and the pump is mounted at a breast level on the human so as to insure that fluid does not leak back to the garment.

6. A Vacuum Assisted Relief System for collecting animal fluid, said system comprising:
   a garment, worn by the animal and contacting at least a portion of the animal where fluid is generated, the garment including at least one hose coupled to the garment, for collecting fluid from the animal;
   a pump, coupled to the hose, for creating a vacuum on the hose to draw fluid from the garment and outputting the fluid from the pump; and
   a receiver, coupled to the pump, for receiving fluid output from the pump,
   wherein the pump further includes a rechargeable battery pack, mounted at breast level on the human, and the receiver is mounted to a leg of the animal, such that the system is entirely mounted to the animal.

7. A Vacuum Assisted Relief System for collecting animal fluid, said system comprising:
   a garment, worn by the animal and contacting at least a portion of the animal where fluid is generated, the garment including at least one hose coupled to the garment, for collecting fluid from the animal;
   a pump, coupled to the hose, for creating a vacuum on the hose to draw fluid from the garment and outputting the fluid from the pump;
   a receiver, coupled to the pump, for receiving fluid output from the pump; and
   a barrier cream, applied to a skin surface of the animal where the garment is worn.

8. A garment for collecting fluids from an animal, the garment, worn by the animal and contacting at least a portion of the animal where fluid is generated, the garment comprising:
   a plurality of layers of material;
   a manifold comprising at least one tube having a plurality of holes formed therein, for collecting animal fluid; and
   a hose having one end coupled to the manifold and the other connectable to a vacuum source, for collecting fluid from the animal,
   wherein the manifold comprises a plurality of tubes having a plurality of holes formed therein, the plurality of tubes being joined by at least one header to the hose such that fluid is collected in the plurality of tubes and drawn into the hose.

9. A Vacuum Assisted Relief System for collecting human urine from an aviator, said system comprising:
   a garment, worn by the aviator and surrounding at least a portion of aviator's crotch, the garment including at least one hose coupled to the garment, for collecting urine from the aviator;
   a pump, mounted to at least one of a survival vest, G-suit, uniform, flightsuit, or jumpsuit, said pump coupled to the hose, for creating a vacuum on the hose to draw urine from the garment and outputting the urine from the pump; and
   a receiver, coupled to the pump, and mounted to the aviator, for receiving urine output from the pump,
   wherein the system is mounted entirely to the aviator such that the aviator may wear the system and enter or exit an aircraft without having to remove or disconnect the system,
   wherein the garment comprises a diaper and the at least one hose includes a manifold loop provided with a plurality of holes in the manifold loop, for receiving urine from the garment.

10. The system of claim 9, wherein the diaper comprises a disposable diaper including a number of layers of material, and the manifold ioop is sandwiched between layers of the disposable diaper.

11. The system of claim 9, wherein the pump comprises a peristaltic action pump creating a vacuum of at least 2 psi.

12. A Vacuum Assisted Relief System for collecting human urine from an aviator, said system comprising:

a garment, worn by the aviator and surrounding at least a portion of aviator's crotch, the garment including at least one hose coupled to the garment, for collecting urine from the aviator;

a pump, mounted to at least one of a survival vest, G-suit, uniform, flightsuit, or jumpsuit, said pump coupled to the hose, for creating a vacuum on the hose to draw urine from the garment and outputting the urine from the pump; and a receiver, coupled to the pump, and mounted to the aviator, for receiving urine output from the pump, wherein the system is mounted entirely to the aviator such that the aviator may wear the system and enter or exit an aircraft without having to remove or disconnect the system, wherein the garment further includes a manifold comprising a plurality of tubes having a plurality of holes formed therein, the plurality of tubes being joined by at least one header to the hose such that urine is collected in the plurality of tubes and drawn into the hose.

13. A Vacuum Assisted Relief System for collecting human urine from an aviator, said system comprising:

a garment, worn by the aviator and surrounding at least a portion of aviator's crotch, the garment including at least one hose coupled to the garment, for collecting urine from the aviator;

a pump, mounted to at least one of a survival vest, G-suit, uniform, flightsuit, or jumpsuit, said pump coupled to the hose, for creating a vacuum on the hose to draw urine from the garment and outputting the urine from the pump; and a receiver, coupled to the pump, and mounted to the aviator, for receiving urine output from the pump, wherein the system is mounted entirely to the aviator such that the aviator may wear the system and enter or exit an aircraft without having to remove or disconnect the system, wherein the pump is mounted at a breast level on the aviator so as to insure that urine does not leak back to the garment.

14. A Vacuum Assisted Relief System for collecting human urine from an aviator, said system comprising:

a garment, worn by the aviator and surrounding at least a portion of aviator's crotch, the garment including at least one hose coupled to the garment, for collecting urine from the aviator;

a pump, mounted to at least one of a survival vest, G-suit, uniform, flightsuit, or jumpsuit, said pump coupled to the hose, for creating a vacuum on the hose to draw urine from the garment and outputting the urine from the pump; and a receiver, coupled to the pump, and mounted to the aviator, for receiving urine output from the pump, wherein the system is mounted entirely to the aviator such that the aviator may wear the system and enter or exit an aircraft without having to remove or disconnect the system, wherein the pump further includes a rechargeable battery pack, mounted at breast level on the aviator and the receiver is mounted to a leg of the aviator, such that the system is entirely mounted to the aviator.

15. A Vacuum Assisted Relief System for collecting human urine from an aviator, said system comprising:

a garment, worn by the aviator and surrounding at least a portion of aviator's crotch, the garment including at least one hose coupled to the garment, for collecting urine from the aviator;

a pump, mounted to at least one of a survival vest, G-suit, uniform, flightsuit, or jumpsuit, said pump coupled to the hose, for creating a vacuum on the hose to draw urine from the garment and outputting the urine from the pump; and a receiver, coupled to the pump, and mounted to the aviator, for receiving urine output from the pump, wherein the system is mounted entirely to the aviator such that the aviator may wear the system and enter or exit an aircraft without having to remove or disconnect the system, further including a barrier cream, applied to a skin surface of the aviator where the garment is worn.

16. A method for collecting animal fluid, said method comprising the steps of:

placing a garment on the animal surrounding at least a portion of the animal where fluid is generated, the garment including at least one hose coupled to the garment for collecting fluid from the animal, creating a vacuum on the hose using a pump to draw fluid from the garment and outputting the fluid from the pump, and receiving fluid output from the pump in a receiver container, wherein the garment comprises a diaper and the at least one hose includes a manifold loop provided with a plurality of holes in the manifold loop, said method further comprising the step of:

receiving fluid from the garment through the plurality of holes in the manifold loop under vacuum from the pump.

17. The method of claim 16, wherein the diaper comprises a disposable diaper including a number of layers of material, and the manifold loop is sandwiched between layers of the disposable diaper.

18. A method for collecting animal fluid, said method comprising the steps of:

placing a garment on the animal and surrounding at least a portion of the animal where fluid is generated, the garment including at least one hose coupled to the garment, for collecting fluid from the animal, creating a vacuum on the hose using a pump to draw fluid from the garment and outputting the fluid from the pump, and receiving fluid output from the pump in a receiver container, wherein the garment further includes a manifold comprising a plurality of tubes having a plurality of holes formed therein, the plurality of tubes being joined by at least one header to the hose such that fluid is collected in the plurality of tubes and drawn into the hose, said method further comprising the step of:

receiving fluid from the garment through the plurality of holes in the manifold loop under vacuum from the pump.

19. The method of claim 18, wherein said step of creating a vacuum comprises the step of creating a vacuum of at least 2 psi.

20. A method for collecting animal fluid, said method comprising the steps of:

placing a garment on the animal surrounding at least a portion of the animal where fluid is generated, the garment including at least one hose coupled to the garment for collecting fluid from the animal, creating a vacuum on the hose using a pump to draw fluid from the garment and outputting the fluid from the pump, and receiving fluid output from the pump in a receiver container, wherein the animal is a human and the pump is mounted at a breast level on the human so as to insure that fluid does not leak back to the garment.

21. A method for collecting animal fluid, said method comprising the steps of:

placing a garment on the animal surrounding at least a portion of the animal where fluid is generated, the garment including at least one hose coupled to the garment for collecting fluid from the animal, creating a vacuum on the hose using a pump to draw fluid from the garment and outputting the fluid from the pump, and receiving fluid output from the pump in a receiver container, wherein the animal is a human and the pump further includes a rechargeable battery pack, mounted at breast level on the human, and the receiver is mounted to a leg of the human, such that the method is entirely mounted to the human.

22. A method for collecting animal fluid, said method comprising the steps of:

placing a garment on the animal surrounding at least a portion of the animal where fluid is generated, the garment including at least one hose coupled to the garment for collecting fluid from the animal, creating a vacuum on the hose using a pump to draw fluid from the garment and outputting the fluid from the pump, and receiving fluid output from the pump in a receiver container, further comprising the step of:

applying a barrier cream to a skin surface of the animal where the garment is worn.

* * * * *